United States Patent [19]

Sheely et al.

[11] 4,230,668

[45] Oct. 28, 1980

[54] PROCESS AND APPARATUS FOR PRODUCING HALOGENATED UNSATURATED HYDROCARBONS

[75] Inventors: Harold R. Sheely, Orleans; F. Frederick Oricchio, Duxbury; Domenic C. Ferrari, Winchester, all of Mass.

[73] Assignee: The Badger Company, Inc., Cambridge, Mass.

[21] Appl. No.: 659,508

[22] Filed: Feb. 19, 1976

Related U.S. Application Data

[62] Division of Ser. No. 493,536, Aug. 1, 1975, abandoned.

[51] Int. Cl.³ .................. B01J 8/22; F27B 15/00; C07C 21/06; C07C 17/04
[52] U.S. Cl. .................. 422/140; 422/142; 422/189; 422/214; 422/240; 422/144; 422/147; 422/227; 422/230; 570/222; 570/226; 570/243
[58] Field of Search ............... 23/260, 284, 288 E, 23/288 S; 260/656, 659; 422/142, 144, 147, 189, 214, 240, 227, 230

[56] References Cited

U.S. PATENT DOCUMENTS

| | | | |
|---|---|---|---|
| 2,378,342 | 6/1945 | Voorhees et al. | 23/288 S X |
| 2,584,391 | 2/1952 | Leffer | 23/288 S |
| 2,602,019 | 7/1952 | Odell | 23/288 S X |
| 2,747,003 | 5/1956 | Kilpatrick | 23/288 E X |
| 2,777,755 | 1/1957 | Eberhardt | 23/260 X |
| 2,838,577 | 6/1958 | Cook et al. | 260/656 |
| 2,858,279 | 10/1958 | Drews | 23/288 S X |
| 2,874,113 | 2/1959 | Smith et al. | 23/284 X |
| 2,943,993 | 7/1960 | Sykes | 23/284 X |
| 3,132,156 | 5/1964 | Lemon et al. | 23/284 UX |
| 3,152,066 | 10/1964 | Wickham | 23/288 S X |
| 3,513,145 | 5/1970 | Crawford | 23/260 X |

Primary Examiner—Michael S. Marcus
Attorney, Agent, or Firm—Schiller & Pandiscio

[57] ABSTRACT

Process and apparatus for producing vinyl chloride monomer characterized by conjoint chlorination and dehydrochlorination reactions carried out in the presence of fluidized solids which provide efficient heat transfer within and between the two reaction zones.

9 Claims, 8 Drawing Figures

PROCESS AND APPARATUS FOR PRODUCING HALOGENATED UNSATURATED HYDROCARBONS

This application is a division of our copending application Ser. No. 493,536, filed Aug. 1, 1975, for Process and Apparatus for Producing Halogenated Unsaturated Hydrocarbons now abandoned.

This invention relates to the production of halogenated hydrocarbons and more particularly to the production of vinyl chloride by a new and improved process.

Vinyl chloride is an important and valuable commercial product which finds numerous uses in the production of polymeric materials. It is commonly produced by the pyrolytic dehydrochlorination of dichloroethanes (1,2 or 1,1 dichloroethane) which may be prepared in one of several ways. Thus, 1,2 dichloroethane, also known as ethylene dichloride (EDC), may be prepared by direct chlorination of ethylene by a gas-phase reaction with chlorine or the reaction of ethylene and chlorine in a liquid medium, while 1,1 dichloroethane can be prepared by the chlorination of ethane. Most commonly, vinyl chloride monomer (VCM) is prepared by dehydrochlorination of 1,2 dichloroethane. The prior art relating to production of the 1,1 and 1,2 dichloroethane isomers and the pyrolytic dehydrochlorination of those isomers to produce vinyl chloride monomer (VCM) is exemplified by U.S. Pat. No. 2,838,577 and British patent Nos. 1,146,706, 1,184,778, 1,218,417, and 1,225,210.

The additive chlorination reactions of ethylene and ethane are highly exothermic and are normally accomplished at near ambient temperatures. Conversely, the dehydrochlorination of dichloroethane is an endothermic reaction requiring a large quantity of heat and a relatively high temperature in order to effect the desired reaction at a desirable rate. This is particularly true of the 1,1 dichloroethane isomer which requires a higher temperature than the corresponding 1,2 isomer to obtain a satisfactory dehydrochlorination rate. The highly endothermic nature of the pyrolytic dehydrochlorination thermal cracking reaction gives rise to a serious problem of supplying additional heat into the body of the reactants at the higher temperature necessarily employed.

The direct chlorination of ethylene or ethane to produce dichloroethanes theoretically yields enough heat to thermally crack the latter to produce monochlorinated hydrocarbons. Accordingly, it has been recognized as desireable to carry out the two reactions in direct succession, i.e., serially, with the process using the heat liberated by the exothermic chlorination addition reaction to supply at least part of the heat requirements of the endothermic cracking reaction while simultaneously providing an internal cooling means for excess heat from the chlorination reaction. Such a process involving conjoint chlorination and dehydrochlorination reactions is disclosed in U.S. Pat. No. 2,838,577 where transfer of heat within and between an exothermic ethane-chlorine reaction zone and an endothermic 1,1 dichloroethane cracking reaction zone is achieved by employing a common fluidized solids reactor bed for both zones. The reactants pass from the chlorination zone to the dehydrochlorination zone and during such transit they are enriched with an additional feed of 1,1 dichloroethane, preferably by recycle of unreacted dichloroethanes from the product stream. The solids employed preferably comprise a selective dehydrochlorination catalyst. However, the process of U.S. Pat. No. 2,838,577 has a number of disadvantages. For one thing, a substantial proportion of the product consists of ethyl chloride. If the solids comprise a dehydrochlorination catalyst, it is possible to produce more vinyl chloride than ethyl chloride, but only by increasing the mole ratio of chlorine to ethane and also by increasing the relative amount of dichloroethane fed to the reactor. If the solids do not comprise a dehydrochlorination catalyst, the product stream will contain substantially more ethyl chloride than vinyl chloride. A second objection is that the product contains a relatively large proportion of unreacted dichloroethane.

It has also been determined that production of dichloroethane by a gas-phase addition reaction of chlorine as described in U.S. Pat. No. 2,838,577 is difficult to control, with the result that undesired polychlorinated hydrocarbon by-products tend to form by direct chloro-substitution of the hydrocarbon feed. Also, the presence of chlorine in the dehydrochlorination reaction zone tends to promote formation of by-products that not only reduce the yield of VCM but which also may be capable of undergoing resinification and coking. Thus the process is not suitable as the basis for a commercial vinyl chloride monomer complex since it is characterized by unsatisfactory vinyl chloride yield and selectivity.

It has been suggested in British Pat. No. 1,218,417 that simultaneous preparation of vinyl chloride and dichloroethanes can be achieved without occurrence of a destructive chlorine-ethylene reaction if 1,1,2-trichloroethane is mixed with ethylene, chlorine and dichloroethanes at selected molar ratios in a mixing zone at a temperature of from 80° C. to 300° C., and then introducing the mixture to a reaction zone that is devoid of any filling and is maintained at a temperature of from 370° C. to 500° C. In this same reference it is noted that destructive chlorination of ethylene may possibly be avoided in a number of ways, e.g. by operating at a reduced pressure, diluting the chlorine with an excess of ethylene or an inert gas, or introducing chlorine at different points of the reactor, but there is a decrease in the productivity of the reactor.

Substantially more satisfactory for the production of VCM is the process described by Joseph A. Buckley, in his article entitled "Vinyl Chloride via Direct Chlorination and Oxychlorination", Chemical Engineering, Nov. 21, 1966, pages 102–104 (see also U.S. Pat. No. 2,724,006 issued to F. Hoechst). A plant embodying the process described by Buckley essentially consists of three units. One is a direct chlorination unit in which EDC is produced by the direct addition of one mol of chlorine to one mol of ethylene. In the second unit, commonly called the cracking unit, one mol of HCL and one mol of vinyl chloride monomer (VCM) are thermally produced per mol of EDC. The third unit, commonly called the oxyhydrochlorination unit (OCHl unit), converts HCl and ethylene into EDC by catalytic oxidation, i.e., two mols of HCl and one mol of ethylene are oxidized with air to make one mol of EDC (the oxyhydrochlorination process is also sometimes referred to as oxychlorination or oxidative chlorination). Theoretically, in a balanced complex, half of the EDC feed to the cracking unit is produced in the direct chlorination unit and the other half in the OHCl unit. Also ethylene feed for the complex is equally divided between the direct chlorination and OHCl units. In practice, however, the direct chlorination unit produces more EDC than does the OHCL unit due to inefficiencies in the overall cycle.

A conventional VCM complex as described by Buckley offers the advantage that it eliminates the manufacture of by-product HCl. However, it has a number of disadvantages including but not limited to relatively high capital equipment costs, excessive production of undesired polychlorinated by-products, and relatively high utilities costs. Other limitations are known to persons skilled in the art.

Accordingly a primary object of this invention is to provide a new process which is an improvement over the above-described processes and other known processes for producing vinyl chloride monomer.

Another primary object of this invention is to provide improved reactor apparatus for use in producing halogenated hydrocarbons.

Another primary object is to provide a process for producing vinyl chloride that utilizes conjoint chlorination and dehydrochlorination processes carried out under conditions that minimize formation of carbonaceous deposits and production of undesired chlorinated hydrocarbon by-products and non-chlorinated hydrocarbons that are capable of undergoing resinification or coking. A further object is to provide a process of the above type wherein the conjoint chlorination and dehydrochlorination reactions are carried out in fluid bed reactor apparatus with a high heat transfer efficiency within and between the two reaction zones. A more specific object is to employ the same fluidized solids for both reaction zones. Another specific object is to avoid the need for using catalyst solids.

Still another object is to provide a process for the production of vinyl chloride wherein hydrogen chloride produced by the dehydrochlorination reaction may be utilized as a chlorinating agent in an oxychlorination stage to produce EDC, whereby substantially no net HCl by-product is formed.

A further object is to provide a process of the character described which avoids the need for a separate direct chlorination reactor and its requirement of a large cooling water capacity.

Other objects are to provide a method of producing VCM which can be carried out with high selectivity and good efficiency at relatively high temperatures and over a relatively wide pressure range.

The foregoing and other objects are achieved by a process of the character described wherein the chlorination and dehydrochlorination reactions are conducted simultaneously with each other in reactor apparatus containing fluidized non-catalytic solids that circulate through and between the two reaction zones so as to remove heat from the exothermic reaction and supply heat to the dehydrochlorination reaction.

A balanced VCM complex embodying the present invention involves oxyhydrochlorination carried out in a first reaction zone according to reaction (1) below and conjoint direct chlorination and dehydrochlorination carried out in a second reaction zone according to reactions (2) and (3) below:

However, as previously noted, production of EDC by a direct high temperature gas phase chlorine addition reaction tends to result in the production of undesired mono- and polychlorinated hydrocarbons. Further, the chlorination reaction may even be destructive of the hydrocarbon feed so that carbonaceous by-products are formed. By way of further explanation of the magnitude of the control problem, a number of secondary reactions (some of which may be desireable, depending upon the product mix desired) can occur in a process for producing VCM employing ethylene and chlorine as starting materials and EDC as an intermediate where the reactants and reaction products are contacted with one another. Some of these possible secondary reactions are as follows:

Also possible are these reactions:

Reaction (10) is a terminal reaction since hexachloroethane cannot be chlorinated further. Thus a specific object of this invention is to provide sufficient reaction control so as to allow only reactions (2) and (3) to occur in the reactor apparatus and to stop such reactions so that reactions (4)–(12) cannot occur. Reactions (11) and (12) are particularly troublesome since they produce carbon which tends to foul up the reactor. Also, reaction (11) causes an excess of HCl to be produced in the system. An excess of HCl will throw the process out of both heat and material balance. In this connection it is to be noted that the problem of excess HCl production occurs in certain commercial VCM processes and in such cases the HCl is used to make other products such as perchloroethylene. However, this is not a fully satisfactory solution since such other products are less valuable than VCM. It is to be noted also that too much HCl converted to EDC results in more heat required for conducting the dehydrochlorination reaction than is available from the direct chlorination reaction. It is recognized that reactions (4)–(10) cannot occur if no chlorine is present, as is true in the cracking furnace of the system disclosed by Buckley (supra). Accordingly, the process of the present invention is designed to precisely control the reaction conditions so as to prevent or suppress undesired reactions of EDC and VCM, primarily reactions (4)–(12), while simultaneously promoting controlled production of EDC and conversion of EDC to VCM.

More particularly, the process comprises feeding chlorine to the chlorination reaction zone at a number of points and in a controlled manner so as to deliberately terminate the direct chlorination and the dehydrochlorination reactions, whereby to minimize formation of carbonaceous deposits and undesired chlorinated hydrocarbon by-products. A further feature of the invention is to recycle chlorinated hydrocarbon by-products to the fluid bed reactor apparatus for thermal dehydrochlorination, whereby to increase the yield of VCM. Still another feature of the invention is to supply carbon tetrachloride to the fluid bed reactor apparatus to (a) serve as a controlled supply of chlorine, (b) stabilize the ethylene feed, and (c) improve the rate of conversion of EDC to VCM. Other features and advantages of the invention are described or rendered obvious by the following detailed description which is to be considered together with the accompanying drawings wherein:

Figure 1:
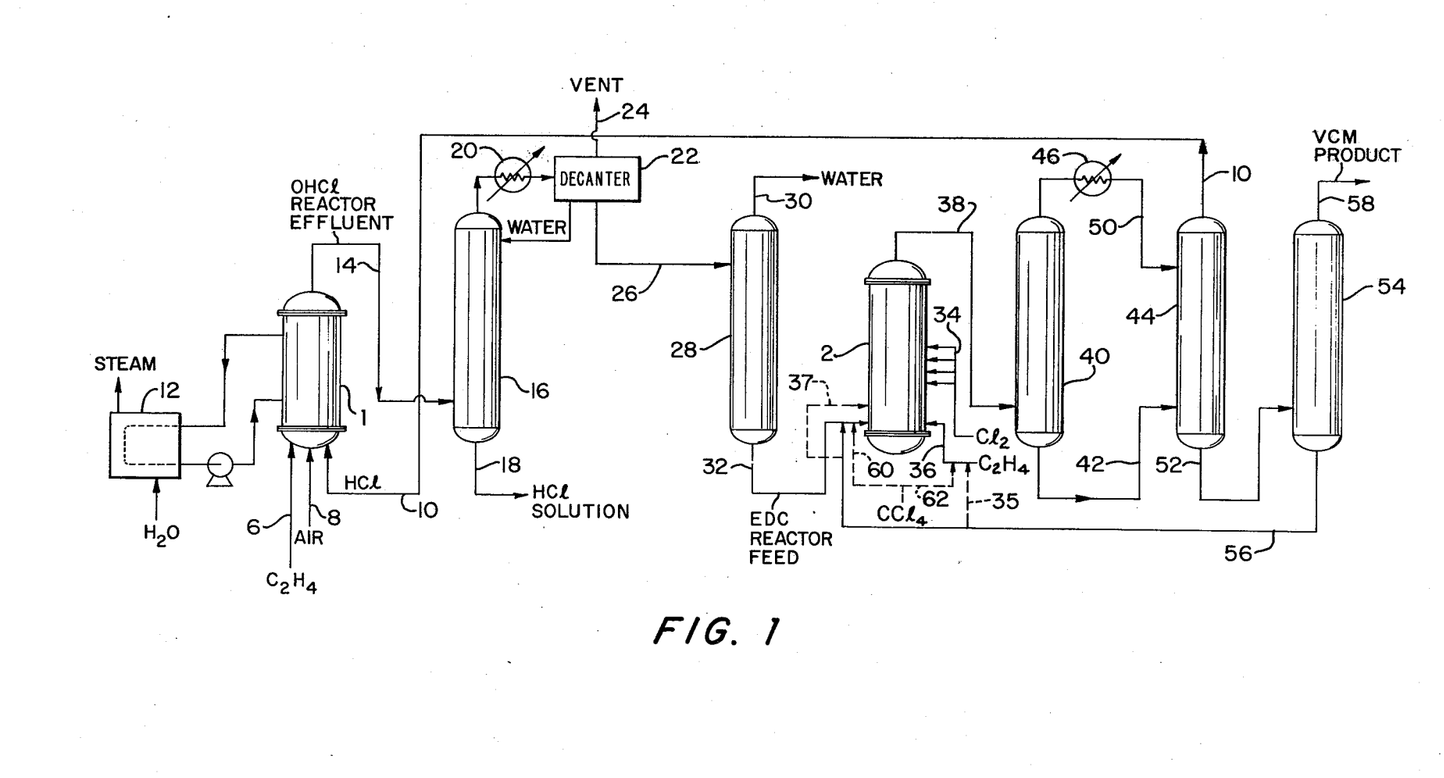
FIG. 1 is a flow diagram illustrating a preferred form of balanced complex for producing vinyl chloride embodying the process of the present invention.

It is to be appreciated that the fluid bed process and apparatus provided by the present invention is not restricted to the specific form of system shown in FIG. 1 and need not be used in conjunction with an oxyhydrochlorination reactor unit, although such conjoint use is preferred because of the desirability and obvious advantages of having a balanced complex wherein the HCl produced by the conversion of EDC to VCM is utilized to produce additional EDC.

Referring now to FIG. 1, the illustrated system comprises a first oxyhydrochlorination reactor 1 for producing EDC and a second reactor 2 for producing VCM. The reactants supplied to reactor 1 are ethylene, air and hydrogen chloride which are delivered via lines 6, 8 and 10 respectively, and the process carried out in reactor 1 is the oxidative chlorination of ethylene according to reaction (1) above. Reactor 1 contains a highly selective oxyhydrochlorination catalyst.

The oxyhydrohalogenation reaction may be carried out in various ways known to persons skilled in the art. Thus, for example, it may be carried out according to the processes described in U.S. Pat. Nos. 3,214,481 and 3,214,482 using an aqueous catalyst consisting of a cupric halide or a ferric halide catalyst component and a promoter component which is a halide of bismuth, copper, chromium, cobalt, iron, mercury, molybdenum, nickel, tin, titanium, vanadium, or manganese. Cupriccuprous choride and ferric chloride are the preferred catalyst systems for oxyhydrochlorination according to the processes of U.S. Pat. No. 3,214,481 and 3,214,482. The oxyhydrochlorination reaction also may be carried out according to the process disclosed in U.S. Pat. No. 3,488,398 using a copper halide catalyst. Preferably in the system of FIG. 1 the oxidative chlorination reaction is carried out in reactor 1 according to the teachings of U.S. Pat. No. 3,448,398 using a fluidized bed of a catalyst which essentially comprises cupric chloride carried on a support of alumina. The reaction is carried out in the vapor phase at a moderate pressure, typically about 10-15 psig. and a temperature in the range of about 190° C. to about 250° C. The heat of reaction is removed by circulating a liquid coolant in a closed circuit which includes cooling coils (not shown) in the reactor and a heat exchanger 12. The liquid coolant is cooled in exchanger 12 by indirect heat exchange with water to produce steam. The reaction effluent is withdrawn from the reactor via a line 14 and passed to an adiabatic quench column 16 where it is separated by adiabatic quenching into a gaseous EDC-rich fraction and a second liquid fraction which is an aqueous HCL solution. The latter is recovered via a line 18. The gaseous EDC-rich fraction is cooled by passage through a heat exchanger 20 and then passed to an EDC recovery unit comprising a decanter 22 where it is separated into a gaseous fraction comprising unreacted ethylene and any off-gases such as oxygen, nitrogen, water vapor, carbon dioxide, and carbon monoxide which are vented via a line 24, plus a liquid or wet crude EDC fraction. This wet crude EDC fraction is passed via a line 26 to a drying column 28.

It also is contemplated that the effluent from reactor 1 could be subjected to a multi-step condensation and extraction treatment as disclosed in U.S. Pat. No. 3,488,398 for recovery of a dry EDC fraction. Thus, although not shown, it is contemplated that the decanter 22 may be replaced by an EDC recovery unit designed so that (a) the overhead from quench column 16 is first passed through one or more stages each consisting of (1) a cooling condenser in which EDC, some water vapor and any low boiling by-products such as ethyl chloride, trichloroethylenes, carbon tetrachloride, and chloroform are condensed and (2) a settling tank in which these condensed materials are separated from the uncondensed vapor, (b) the uncondensed vapor is contacted in an absorber column with a selected liquid absorbing medium (such as toluene) so as to effect absorption of any remaining EDC and $C_1$-$C_3$ chlorinated hydrocarbons, and overhead separation of water vapor and condensed off-gases, and (c) the enriched absorbing medium is passed to a stripper where the absorbed EDC and other chlorinated hydrocarbons are separated from the absorbing medium which is recycled to the absorber column. The EDC and other chlorinated hydrocarbons recovered by these condensation and absorption treatments are combined and fed to drying column 28. In drying column 28 the crude EDC fraction is dried so as to produce an overhead fraction consisting of water and a moisture-free EDC-rich bottoms fraction. The overhead water fraction is withdrawn by line 30 and the dry EDC bottoms fraction is recovered and introduced as a feed to reactor 2 via line 32.

As explained more fully below, reactor 2 contains a bed of selected non-catalytic solids which are fluidized and function as a heat transfer medium. Line 32 leads directly into one reaction chamber of the reactor. Also supplied to a second reaction chamber of reactor 2 via supply lines 34 and 36 are quantities of chlorine and ethylene. These latter materials are reacted in reactor 2 to form EDC according to the direct chlorination reaction (2) above. As explained in greater detail below in connection with FIGS. 2 and 3, the EDC formed according to reaction (2) above and the EDC feed supplied via line 32 are thermally cracked in reactor 2 to produce vinyl chloride monomer according to the thermal cracking reaction (3) above. A substantial portion of the thermal energy required to carry out reaction (3) is provided by the heat given off by reaction (2).

The reaction effluent from reactor 2 is carried via a line 38 to a quench column 40 where it is separated by quenching into a liquid bottoms fraction containing EDC and other heavies and an overhead gas fraction rich in ethylene, HCl and VCM. The bottoms fraction is passed via a line 42 to a distillation column 44. The overhead fraction from column 40 is cooled in a heat exchanger 46 and passed via a line 50 to the top section of distillation column 44. The latter is operated so as to produce an overhead fraction consisting of HCl and ethylene gas which is recycled via line 10 to reactor 1, and a crude vinyl chloride bottoms fraction. The latter is passed via a line 52 to a vinyl chloride distillation column 54 which is operated so as to produce an overhead fraction consisting of at least about 98% VCM and a bottoms fraction that contains any unreacted EDC plus any by-products such as other chlorinated hydrocarbons having a boiling point higher than vinyl chloride monomer. This bottoms fraction is preferably recycled via a line 56 to reactor 2. It may be introduced to reactor 2 with the crude EDC delivered by line 32 or with the ethylene delivered by line 36 or separately via line 37. It can also be introduced along with the ethylene via line 35. These recycled by-products tend to improve the yield of VCM produced in reactor 2. The overhead VCM product stream recovered from column 54 is delivered to storage via a line 58.

To further improve conversion of EDC to VCM, it is preferred to feed carbon tetrachloride in controlled amounts to reactor 2 via a line 60 together with the EDC delivered via line 32. Optionally, as an additional control measure, carbon tetrachloride also may be fed via a line 62 to the reactor together with the ethylene feed.

As explained more fully hereafter in conjunction with FIGS. 3-8, reactor 2 consists of three connecting reaction chambers or zones as follows: (1) an EDC cracking section where EDC from the reactor 1 is thermally cracked to VCM at high per pass conversion, (2) an ethylene-chlorine reaction section where the $C_2H_4$ and $Cl_2$ are reacted in a controlled manner to produce primarily EDC and VCM and (3) a post-cracking section where the effluents from the first and second sections are combined and the thermal cracking of EDC is carried to completion. The exothermic heat of reaction in the ethylene-chlorine section is transferred to the two cracking sections by a continuously circulating stream of fluidized solids and used therein to supply the endothermic heat required to satisfy the EDC cracking reaction.

In the development of this invention, it has been determined that the chlorine addition reaction is not particularly specific as to which of the double bonds it will attack in a mixture of ethylene and unsaturated chlorohydrocarbons (e.g. by reactions 2, 4, 6, 8 and 10). Also, the chlorine addition reaction is very fast compared to the dehydrochlorination reactions (e.g. reactions 3, 5, 7 and 9) and chlorine is a strong catalyst for dehydrochlorination. On the other hand, ethylene is a strong inhibitor for dehydrochlorination and is a mild catalyst for the EDC degradation (reaction 11) which is relatively slow compared with dehydrochlorination reactions. It also has been determined in the course of developing the present invention that in a direct chlorination reactor in order to achieve a chlorine selectively to EDC and VCM of about 90%, it is necessary to maintain an ethylene to chlorine mol ratio in excess of 4:1. At unity mol ratio, chlorine selectivity to EDC and VCM is less than about 40%. A conventional balanced EDC-VCM complex of the type involving both an oxyhydrochlorination unit and a direct chlorination unit (see Buckley supra) requires 2 mols of ethylene per mol of chlorine, with about half of the ethylene being fed to the oxyhydrochlorination unit. Using a fluid bed reactor constructed in accordance with this invention, all of the ethylene could be used as feed to the ethylene-chlorine section and any unreacted ethylene could then be separated and fed to the oxyhydrochlorination reactor 1 in admixture with HCl. However, with an ethylene to chlorine feed ratio of 2:1, it has been found that such procedure would result in chlorine selectively to EDC and VCM of less than about 65%. Furthermore, the HCl/VCM ratio would be considerably in excess of 1.0. From a strictly commercial standpoint, a chlorine to EDC and VCM selectivity of about 65% is unsatisfactory. Moreover, with a high ethylene/chlorine feed ratio, the heat balance around the fluid bed reactor would require a very high temperature level of heat input from an external source. This would defeat a purpose of this invention which is to eliminate or minimize fuel requirements of the reactor.

The problem of maximizing chlorine selectively to EDC and VCM while minimizing fuel requirements for the reactor is solved according to the present invention by adding chlorine incrementally to the ethylene-chlorine reaction section of the fluid bed reactor via multiple chlorine injection ports. The ethylene/chlorine ratios at each injection port is kept high purposely but the overall ethylene/chlorine feed ratio is kept below about 2:1. In this manner by-product formation by undesired chlorination reactions is minimized and EDC production is maximized. By closely spacing the chlorine injection ports, a very short residence time is provided which is sufficient to allow the chlorine addition reaction with ethylene to proceed essentially to completion but yet reduce the degree of any accompanying dehydrochlorination reaction. This short residence time helps keep the degradation reactions at a low level. Additionally, the inhibitive action of ethylene offsets the catalytic effect of chlorine with respect to dehydrochlorination. In a balanced complex as shown in FIG. 1, about one-half of the total ethylene feed is fed to the ethylene-chlorine section of the fluid bed reactor while the remainder is fed to the oxyhydrochlorination reactor 1. Hence, the heat input requirements of the fluid bed reactor are minimized.

Figure 2:
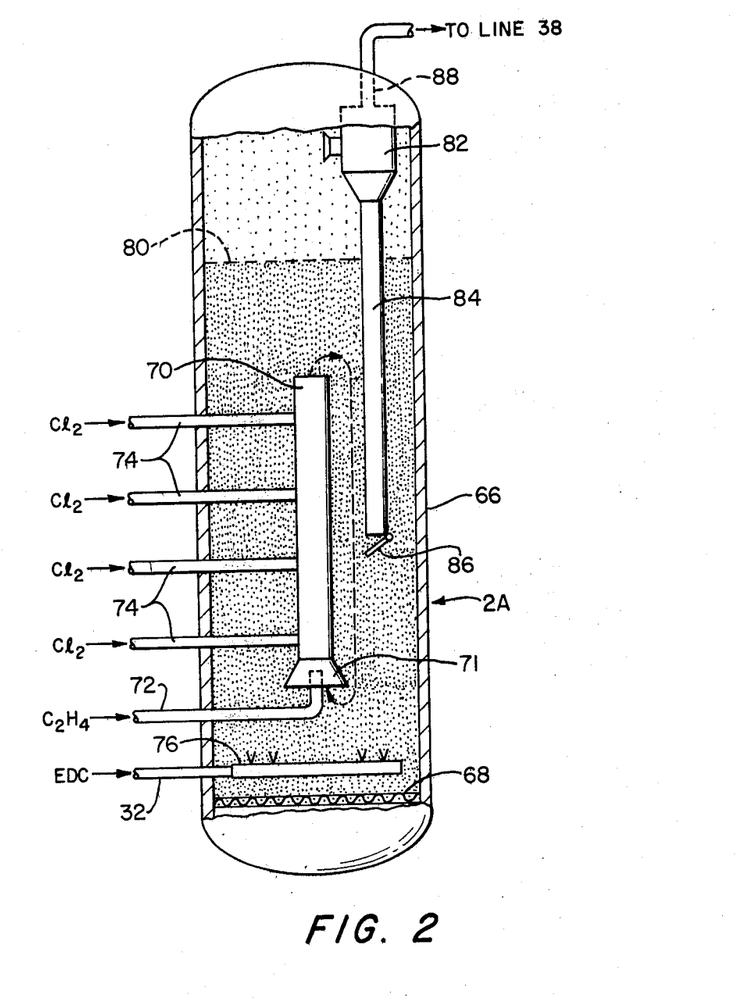
FIG. 2 illustrates a preferred form of fluid bed reactor in which chlorination and dehydrochlorination reactions are carried out simultaneously in accordance with the invention.

A fluid bed reactor unit satisfying the requirements of this invention may take various forms. The preferred form of reactor is shown in FIG. 2. In this case, the reactor unit, identified generally as 2A, comprises a vessel 66 preferably provided with a fixed grid 68 which supports a bed of non-catalytic solids of selected particle size and composition. Mounted within the vessel is a riser assembly which comprises a riser tube 70 that is open at both ends and is supported by suitable means such as struts (not shown) attached to the wall of the vessel. Preferably the bottom end of the tube has a flared shroud 71 to facilitate inflow of solids. A feed tube 72 has one end projecting up into the shroud and its other end leads out of the side of the vessel and is connected to ethylene feed line 36. The upper end of the riser tube terminates well below the upper end 80 of the fluidized bed of solids. Riser tube 70 also has a plurality of side ports that are connected by separate feed tubes 74 to chlorine feed line 34. The EDC feed line 32 is connected to another inlet port in vessel 66 that is located immediately above grid 68 and is connected to a distribution assembly 76 designed to uniformly inject the EDC feed into the bed of solids but outside of the riser. A cyclone separator 82 is mounted in the solids disengaging zone above the bed of solids and has a dipleg 84 that extends down into the bed of solids. The bottom end of dipleg 84 preferably is fitted with a flapper valve 86 (or other suitable baffle). The cyclone has an effluent outlet tube 88 that is connected to line 38. As is obvious, the cyclone separates fines from the reactor effluent and returns the same to the bed of solids.

The solids are fluidized outside of the riser tube by the EDC supplied by distributor 76 and inside the riser tube by the ethylene feed supplied via line 36. The solids circulate up through the riser and down again outside the riser in the manner shown by the broken line arrow, and this circulation mode is accomplished by the pumping action of the ethylene. In this reactor, the interior of the riser comprises the ethylene/chlorine reaction section mentioned previously. The aforementioned post-cracking section extends from about the upper end of the riser tube to the top of the fluidized bed while the EDC cracking section extends from the post-cracking section down to about the point where the EDC feed is introduced into vessel 66. The post-cracking section is sized to provide a large holdup to complete the thermal dehydrochlorination of EDC to VCM.

Although not shown, heating coils may be provided for the reactor to bring the bed of solids up to a suitable temperature level to initiate dehydrochlorination of the EDC and depending upon reactor heat losses, to supplement the heat transferred to the dehydrochlorination reaction from the direct ethylene chlorination reaction. Preferably, however, heat balance in the reactor is maintained by adding heat in the form of feed preheat. At the low feed ratios employed, combined with the high per pass conversion of EDC, this preheat can be supplied by high pressure steam or by process heat exchange, thereby eliminating the need for fuel gas or other outside sources of high temperature level heat.

Operation of reactor 2 in the practice of this invention is as follows: (1) ethylene and chlorine are reacted stepwise in the riser tube to produce EDC and heat, (2) the exothermic heat of reaction in the riser tube is transferred to the post-cracking section and also the EDC cracking section by a continuously circulating stream of fluidized solids, (3) EDC delivered from reactor 1 is thermally cracked in the EDC cracking section with the endothermic heat required to satisfy the cracking reaction being supplied by the heat transferred from the riser tube, and (4) the effluents from the ethylene-chlorine reaction section and the EDC cracking section are combined in the post-cracking section where thermal cracking of EDC is carried essentially to completion under the influence of heat transferred from the riser tube. In practice, some of the EDC formed in the ethylene-chlorine reaction section tends to be cracked to VCM in the upper end of the riser tube due to the accumulation of heat generated by the direct chlorination reaction. However, since ethylene is an inhibitor for the dehydrochlorination and because the ratio of ethylene to chlorine is deliberately kept high at the various chlorine injection points, the relative amount of EDC that is cracked in the riser tube is quite small.

It is to be noted that the overall ethylene-to-chlorine ratio in the riser tube must be kept low so that the amount of ethylene entering the post-cracking chamber will be at a minimum. Otherwise, the EDC in the post-cracking section will be strongly induced to make carbon, e.g., by reaction (11) above. Reaction (11) appears to be promoted strongly by ethylene and to occur to a significant extent even at temperatures as low as 500° F. This EDC degradation reaction is minimized by so controlling the amount of chlorine fed in at each riser inlet that substantially all of the ethylene reacted in the riser tube is converted to EDC.

The solids serve merely as a heat transfer medium and should not have any catalytic properties. In fact, it has been determined that if catalyst type solids, i.e., solids comprising active sites, are used, they tend to promote carbon-forming reactions. Accordingly, solids with few or no active sites are used in the practice of this invention. To assure satisfactory operation, the solids are preconditioned to neutralize any active sites. This is achieved by coating the solids with carbon so as to choke off the active sites. The preconditioning is achieved by operating the reactor under normal operating conditions. Carbon is formed during the initial phase of operation and is deposited on the solid particles. The amount of time required to equilibrate, i.e., precondition, the solids is a function of the surface area of the solids. For high surface area solids, preconditioning may take one or more days, while with low surface area solids, equilibration can be accomplished in a matter of hours. It has been found also that the mol ratio of HCl to VCM produced in the fluid bed reactor increases with larger surface area solids and that for best results the solids should not have a surface area in excess of about 50 square meters per gram. Accordingly, low surface area solids are preferred. As used herein, the term "low surface area solids" denotes solids having a surface area of less than about 50 square meters per gram. Various solids may be used in the practice of this invention, including but not limited to silica, alumina, silica-alumina, glass powder, and carbon. Preferably, but not necessarily, the solids have a particle size of about 50-70 microns average diameter.

An important advantage of the process is that the fluid bed reactor 2 can be operated at temperatures as high as 1000° F. and at pressures up to about 300 psig. The minimum reactor temperature for satisfactory operation is about 700° F. The best results are achieved with a temperature in the range of about 840° F. to about 925° F. The reactor may be operated at pressures as low as atmospheric pressure but preferably it is operated at pressures between about 50 and about 250 psig.

The vessel of reactor 2 is preferably made of nickel or a nickel alloy (e.g. type 304 stainless steel) as a protection against chlorine attack at the elevated temperatures maintained in the reactor. However, a carbon steel vessel lined with nickel, a nickel alloy, ceramic or brick also may be used. The riser (or the external reaction chamber or transfer line, if used) is made of an erosion resistant material, e.g. a nickel-containing alloy such as type 304 stainless steel). Preferably the riser is made of a ceramic material. By way of example but not limitation, the riser may be made of alumina.

The velocity of the gas flow up through the bed outside of the riser and also up inside the riser are adjusted so as to maintain the solids in both chambers in a dense phase. Alternatively, the solids within the riser may be maintained as a dilute phase. For the purpose of this invention, a fluidized solids distribution of about 10-40 lbs./cubic foot constitutes a dense phase. However, the process has been operated successfully with a dilute phase in the riser of between 0.02 and 0.5 lbs./cubic foot. Gas velocities of between about 0.7 to 3.0 feet/second are used to fluidize the solids outside of the riser as a dense phase, while gas velocities of between about 5 to 40 feet/second are required to cause the solids to flow up in the riser as a dense phase. A feature of this invention is that relatively short residence times may be used, particularly in the riser. The residence time in the riser is kept short enough to permit making EDC but not VCM in the bottom of the riser tube, since otherwise, the VCM may tend to become chlorinated and thereby produce undesired by-products.

Figure 3:
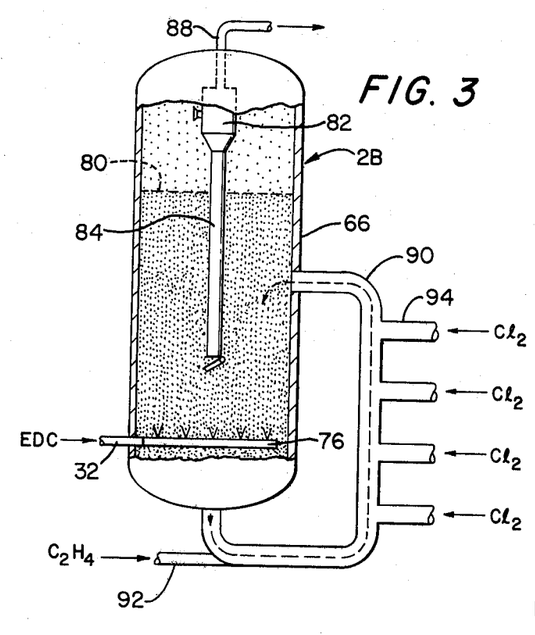
FIGS. 3-8 illustrate other forms of fluid bed reactors and modifications that can be used to practice the invention.
Figure 4:
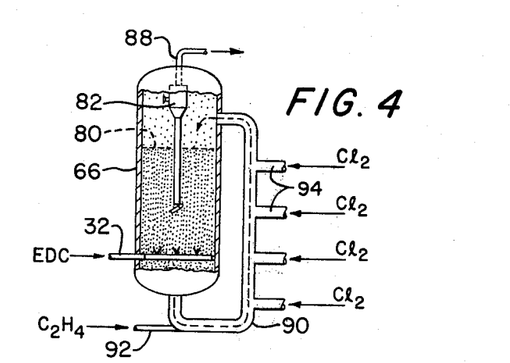
Figure 5:
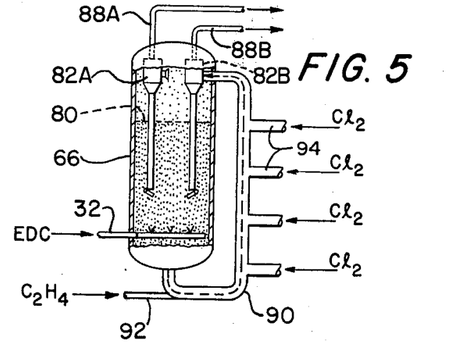

The chlorine injection ports provided in the riser may vary in number and spacing and more than one may be provided at any given location along the length of the riser. At least two, and preferably about four injection ports are provided along the riser. More preferably between about six to nine injection ports may be provided along the riser. More than nine injection ports may be provided but are not preferred due to the high number of feed tubes required. Depending upon the spacing of the ports, the chlorine may be injected at the same or different rates at the several ports. Further by way of example, the ports and the rates of flow at the ports may be adjusted so as to provide equal residence times for gas flow between one injection port and the next injection port. Since each additional chlorine input serves to increase the gas velocity in the riser, it is necessary for the attainment of equal residence time to have the spacing between ports increase with the increasing distance from the bottom of the riser, or with increasing distance along the direction of flow of solids in the transfer line in the case of a reactor as shown in FIGS. 3-5. Alternatively, the riser tube diameter may be varied so as to maintain constant gas velocity therein.

The overall feed ratio in mols of ethylene to chlorine in the riser is maintained between about 0.8:1 and about 2.0:1. However, the rate of introduction of chlorine at the several injection ports is such as to maintain in the riser at the lowest port an ethylene to chlorine mol ratio in excess of about 2:1 and preferably at least about 4:1, and at the highest port a mol ratio of at least about 1:1 and preferably at least about 2:1. In practice, the ratio of ethylene/chlorine at the highest port may not be maintained at 2:1 or higher and tends to be lower than at the preceding port or ports due to the fact that the overall feed ratio is less than about 2.0:1 and also because a majority of the ethylene introduced to the riser has been converted to EDC by reaction with chlorine introduced downstream of the highest port. Nevertheless, by controlling the overall ethylene/chlorine feed ratio and the rate of introduction at each port as just described, it has been found possible to achieve a selectivity of ethylene to EDC and VCM of more than 90%.

The mol ratio of EDC introduced directly to the bed of solids outside of the riser and the ethylene feed to the riser preferably is set so that the amount of heat released by the conversion of ethylene to EDC is slightly in excess of the amount of heat required to thermally crack the EDC supplied to the reactor and the EDC produced in the riser. In practice, 1 mol of EDC is fed to the reactor for each mol of ethylene fed to the riser. However, an EDC/ethylene ratio smaller or greater than unity may also be used provided appropriate measures are taken to maintain the proper heat balance.

The internal riser assembly is not essential to the invention and may be replaced by an external transfer tube. This modification is exemplified by reactor 2B shown in FIG. 3. In this case the vessel 66 is provided with a transfer tube 90 that leads from an outlet in the bottom of the vessel to an inlet in the side of the vessel below the level 80 to which the bed of solids is fluidized. Transfer tube 90 has a first injection port provided with an inlet tube 92 which is connected to the ethylene feed line, and a plurality of spaced injection ports provided with inlet tubes 94 which are connected to the chlorine feed line. The grid 68 is omitted and the solids in the vessel are fluidized by the EDC fed in via distributor 76. In this form of reactor, the ethylene feed fluidizes solids in the transfer line and also provides the necessary pumping action to cause the solids to flow out of the bottom of the reactor vessel up along the transfer line and back into the vessel. This circulation path is indicated by the broken line arrow in the drawing. This reactor is operated in the same manner as a reactor with an internal riser. The transfer tube constitutes the direct chlorination reaction section and the volume of solids above the point where the transfer line returns solids to the vessel constitutes the post-cracking section or zone.

FIG. 4 shows a modification of the apparatus of FIG. 3 which also is operated in the same manner as a reactor with an internal riser. In this modification the transfer line 90 is arranged so as to return the solids into the reactor above the level 80 of the fluidized bed. In this case the post-cracking section of the vessel 66 is the upper end of the bed of solids therein and for the direct chlorination reaction it is that portion of the transfer line between the last chlorine injection port and vessel 66.

FIG. 5 shows still another modification. In this case the reactor unit is like the one shown in FIG. 4, except that two cyclone separators 82A and 82B are provided. The inlet of separator 82A is disposed to receive the reaction effluent passing up out of the bed of solids in vessel 66, while the inlet of separator 82B is connected to transfer line 90 so as to receive the direct chlorination reaction effluent. The outlet lines 88A and 88B of the two separators are connected to line 38 leading to column 40. The post-cracking section is the same as for the reactor of FIG. 4.

Figure 6:
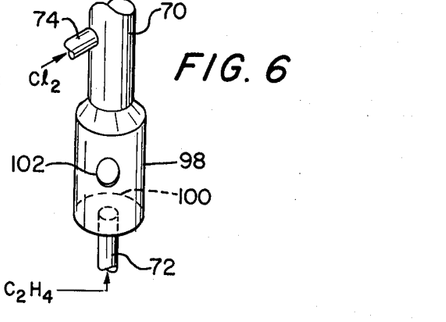

FIG. 6 shows another possible modification of the internal riser assembly. In this case the bottom of riser tube 70 has an enlarged hollow eductor section 98 that has a solid bottom wall 100 provided with an inlet port to which is connected the ethylene feed tube 72. The side wall of the eductor section has one or more enlarged openings 102 through which the solids in the vessel 66 can flow into the riser. The stream of ethylene fed into the bottom of the eductor section induces solids flow through opening 102 and carries them up through the riser. It is understood of course, that the riser has a plurality of chlorine inlet ports like the riser shown in FIG. 2.

Figure 7:
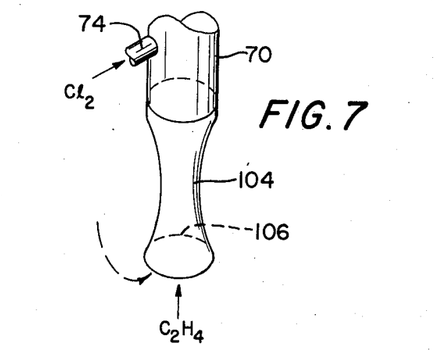

It also is contemplated, as shown in FIG. 7, that the bottom end of riser tube 70 may be provided with a venturi mixing nozzle in the form of a tapered reduced diameter throat section 104 and an open flared or bell end 106. The ethylene feed tube 72 projects up inside the flared bottom end 106. The latter is made large enough in diameter so that solids can flow into it around feed tube 72. The ethylene stream delivered by feed tube 72 provides the necessary pumping action to draw solids into the bottom end of the riser from the surrounding bed and carries the solids up through the riser so as to provide circulation as described in connection with FIG. 2. The throat section 104 acts as a venturi mixing nozzle so that the solids are uniformly dispersed in the ethylene feed stream. Alternatively, the throat section 104 may be spaced from the lower end of the riser so that solids will be drawn up into the riser through the gap between the section 104 and the riser.

Figure 8:
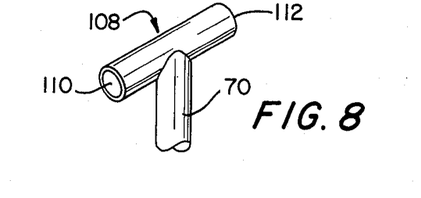

FIG. 8 shows one way that the upper end of riser 70 can be modified. In this case the upper end of riser 70 terminates in a hollow "T" or "Tee" section 108 which provides two oppositely and horizontally directed discharge ports 110 and 112. These ports act to discharge solids and reaction effluent laterally rather than vertically into the reactor vessel 66. The "tee" section 108 is normally submerged in the bed of solids and its lateral discharge acts to maximize the time that the direct chlorination reaction effluent is in the post-cracking section.

It is to be appreciated that the external transfer line 90 functions as a separate reactor and, therefore, it is contemplated that the transfer line could be replaced by a second vertically elongate reactor vessel with a first lower line connecting the bottom of this second vessel with the bottom of reactor vessel 66 and a second upper line connecting the top of the second vessel to a side port in vessel 66 located either below or above the upper surface 80 of the bed of solids. Ethylene injected either into the first connecting lne or directly into the bottom of the second vessel would provide the necessary pumping action to cause the solids to flow from the bottom of vessel 66 into the bottom of the second vessel, and the solids in the second vessel would be transferred back into vessel 66 via the second connecting line under the driving influence of the reaction effluent of the second reactor vessel.

As indicated earlier, the overall conversion of EDC to VCM is enhanced by the addition of carbon tetrachloride to the EDC cracking section. This added $CCl_4$ inhibits formation of carbon from the EDC via reaction (3) and also provides chlorine which catalyzes dehydrochlorination of EDC to form VCM. However, it has been found that in order for the $CCl_4$ to enhance conversion of EDC to VCM, it must be introduced to the reactor vessel in an amount between about 0.7 and 3.3 mols per 100 mols of EDC. Above about 3.3 mols is avoided for reasons of economy. The amount of $CCl_4$ required to be added decreases with increasing reactor temperature. It has been found that with addition of $CCl_4$, it is possible to increase the overall conversion of EDC to VCM to over 90% and the selectivity also is in excess of 90%. It has been found also that adding chlorine instead of carbon tetrachloride to the reactor produces no similar beneficial results.

It also is contemplated to add $CCl_4$ to the ethylene feed line when the feed line is constructed of nickel or a nickel-containing alloy and the ethylene feed is heated to about 300° F. This has been found to be beneficial in that it stabilizes the ethylene so that it will not form carbon and methane in the feed line. The amount of $CCl_4$ delivered to the riser or the external transfer line should be maintained between about 0.5 and about 4.0 mols per 100 mols of ethylene.

The following examples illustrate the method of the present invention and certain aspects thereof. Except as noted otherwise in each of the following examples the reactor employed was of the internal riser type illustrated in FIG. 2. The reactor vessel was made of nickel and the riser was made of fired 99+% pure alumina. The reactor vessel had a height of six feet and an internal diameter of about two inches. The vessel contained a bed of alumina silicate solids and the bed height was about 2.5 feet. The solids had a particle size in the range of between about .44μ and 150μ, and had an average surface area of about 4 square meters/gram. The chemical composition of the solids was about 60% $SiO_2$ and 40% $Al_2O_3$ by weight. The riser had a length of 18 inches, an internal diameter of about ⅜ inch, and eight chlorine injection ports located as follows:

| PORT NO. | LOCATION |
|---|---|
| 8 | 3 inches below top |
| 7 | 2¾ inches below No. 8 |
| 6 | 2½ inches below No. 7 |
| 5 | 2¼ inches below No. 6 |
| 4 | 2 inches below No. 5 |
| 3 | 1¾ inches below No. 4 |
| 2 | 1½ inches below No. 3 |
| 1 | 1¼ inches below No. 2 |

The reactor vessel was jacketed with a fused salt bath contained in the chamber formed between the vessel and jacket. An electrical heating coil surrounded the jacket.

EXAMPLE I (Sample Runs #168–177)

EDC was fed into the reactor at a rate of 4.71 gm mols per hour and a temperature of about 400° F. Also fed with the EDC was 0.10 gm mols/hr $CCl_4$, 0.28 gm mols/hr trans-1,2-dichloroethylene, 0.03 gm mols/hr chloroform, and 0.05 gm mols/hr perchloroethylene. Ethylene and chlorine were fed into the riser at rates of 3.55 and 2.44 gm mols per hour and a temperature of about 250° F. The reactor was operated at about atmospheric pressure and at about 890° F. The chlorine flow was equally split between the eight ports. The ethylene contained 0.19 gm mols $CCl_4$. Also, 1.33 gm mols/hr of nitrogen was fed to the reactor with the EDC. The run lasted 60 hours. The effluent from the reactor was recovered and analyzed. An initial sample of the effluent was taken about 1 hour after startup and additional samples were taken about 5–8 hours apart. The feed and effluent compositions are shown in Table I.

TABLE I

| | (gm mols/hr) | | | |
|---|---|---|---|---|
| | Feed | Effluent Initial Sample | Effluent Final Sample | Effluent Average |
| EDC | 4.71 | 0.15 | 0.31 | 0.15 |
| Nitrogen | 1.33 | 1.57 | 1.18 | 1.33 |
| Ethylene | 3.55 | 1.35 | 1.59 | 1.55 |
| Chlorine | 2.44 | — | — | — |
| VCM | — | 7.52 | 6.13 | 6.96 |
| Carbon Tetrachloride | 0.29 | 0.21 | 0.47 | 0.34 |
| cis & trans 1,2-dichloroethylenes | 0.28 | 0.23 | 0.32 | 0.32 |
| Vinylidene chloride | — | 0.11 | 0.14 | 0.16 |
| Hydrogen Chloride | — | 8.99 | 7.34 | 8.48 |
| Chloroform | 0.03 | 0.03 | 0.06 | 0.05 |
| Trichloroethylene | — | — | — | NIL |
| Perchloroethylene and others | 0.05 | 0.04 | 0.07 | 0.05 |
| TOTAL | 12.68 | 20.20 | 17.61 | 19.39 |

From the average of the samples taken it was determined that EDC conversion was 97.3% and $C_2$ selectivity to VCM was 94.5%.

EXAMPLE II (Sample Run #145)

In this example the reactor and solids were the same as in Example I. EDC and carbon tetrachloride were fed together into the main part of the reactor at rates of 7.67 and 0.21 gram mols/hr respectively. Simultaneously ethylene and carbon tetrachloride were fed into the bottom of the riser at respective rates of 8.75 and 0.39 gram mols/hr, and chlorine (at a total feed rate of 7.68 gram mols/hr) was fed into the eight riser ports at equal rates. The EDC, ethylene and chlorine were preheated to the same temperature as in Example I and the reactor was operated at about 890° F. and about 1.5 atmospheres (abolute) pressure. The run lasted about 44 hours. A sample of the effluent was taken 1 hour after startup and thereafter additional samples were taken periodically. Sample Run #145 was taken at about 33 hours after startup. The composition of Sample #145 is presented in Table II.

TABLE II

|  | (gm mols/hr) EFFLUENT (run #145) |
| --- | --- |
| EDC | 0.3658 |
| Ethylene | 3.5279 |
| Chlorine | — |
| VCM | 13.4812 |
| Carbon Tetrachloride | 0.3459 |
| cis & trans 1,2-dichloroethylenes | 0.0912 |
| Vinylidene Chloride | 0.1496 |
| Hydrogen Chloride | 17.8000 |
| Chloroform | 0.0422 |
| Perchloroethylene & others | 0.0643 |

From Sample #145, it was determined that EDC conversion was about 95.2% and $C_2$ selectivity to VCM was about 97.9%.

The purpose of Examples III through V is to show the marked superiority of carbon tetrachloride over chlorine as an additive for improving per pass conversion of EDC.

In these three examples, the reactor had the same construction as the one employed for the previous examples, but its internal diameter was only 1¼ inch. The riser was not used. The solids were similar to that used in the previous examples but only about 600 cc were employed.

EXAMPLE III (Run #348)

EDC preheated to about 400° F. was fed into the reactor at a rate of 2.82 gm mols/hr. The reactor was heated to a temperature of 900° F. The reactor effluent was recovered and analyzed. From Sample #348 it was determined that EDC conversion was 57% and $C_2$ selectivity to VCM was 93.5%.

EXAMPLE IV (Run #410)

EDC preheated to about 400° F. was fed into the reactor at a rate of 3.41 gm mols/hr. The reactor was heated to 875° F. Chlorine, at a rate of 0.007 gm mols/hr, was added to the EDC. The reaction effluent was sampled and from analysis of sample run #410 it was determined that the conversion of EDC was 85% and $C_2$ selectivity to VCM was 94.0%.

EXAMPLE V (Runs #897-898)

EDC preheated to about 400° F. was fed into the reactor at a rate of 2.91 gm mols/hr. The reactor was heated to 905° F. Carbon tetrachloride at a rate of 0.076 gm mols/hr, was fed with the EDC. The reaction effluent was sampled and from sample runs #897 and 898 it was determined that the EDC conversion was 99.7% and the $C_2$ selectivity to VCM was 94%.

In the following Examples VI and VII, the reactor and solids were the same as used in Examples III thru V. There was no riser. The ethylene feed line was made of 316 stainless steel. The purpose of these tests is to show the beneficial effect of carbon tetrachloride in reducing the tendency for carbon formation with its resultant equipment pluggage.

EXAMPLE VI (Run #434)

Ethylene, at a rate of 2.54 gm mols/hr and at about 200° F. was fed into the reactor which was heated to 890° F. Chlorine, at a rate of 1.31 gm mols/hr, and at about 200° F., was fed separately into the reactor. Within about eight hours, the reactor was shut down because of pluggage from carbon.

EXAMPLE VII (Run #462)

Ethylene, at a rate of 1.49 gm mols/hr and at about 200° F., was fed into the reactor which was heated to 900° F. Carbon tetrachloride was introduced along with the ethylene feed at a rate of 0.037 gm mols/hr. Chlorine, at a rate of 0.85 gm mols/hr and at about 200° F., was fed separately into the reactor. A pressure increase from carbon deposition did not occur until 48 hours later, but full plugging did not occur.

EXAMPLE VIII (Runs #1984-1984A)

In this example the reactor and solids were the same as used in Example I. The EDC was fed into the reactor at a temperature of 400° F. The reactor temperature was 900° F. Ethylene and chlorine were fed into the riser at a temperature of about 250° F. The chlorine flow was equally split between the eight ports of the riser. The EDC, ethylene and chlorine feed rates were 3.378, 3.390 and 3.263 gm mols/hr respectively. The run lasted 20 hours. The effluent from the reactor was recovered and analyzed at intervals. The composition of the effluent for Sample Runs 1984 and 1984A averaged as shown in Table III.

TABLE III

|  | (gm mols/hr) |
| --- | --- |
| 1,2 dichloroethane | 0.655 |
| 1,1 dichloroethane | 0.0 |
| ethylene | 1.590 |
| hydrogen chloride | 7.876 |
| nitrogen | 0.324 |
| vinyl chloride | 4.198 |
| dichloroethylene | 0.162 |
| methane | 0.0 |
| chloroform | 0.005 |
| carbon tetrachloride | 0.0 |
| trichloroethylene | 0.187 |
| perchloroethylene & others | 0.015 |

The conversion of EDC was about 80.6% and the selectivity of $C_2$ to VCM was about 90%.

Examples I and II are illustrative of (a) the addition of $CCl_4$ to both the ethylene and EDC feeds for reactor 2, and (b) non-uniform spacing of the chlorine injection ports. Example I also simulates recycle of by-products to reactor 2 from VCM column 54 via line 56 since it includes compounds of the type that tend to occur as by-products during formation of EDC and conversion of EDC to VCM. Example I also demonstrates that $C_1$-$C_3$ chlorinated by-products and unreacted ethylene and EDC in the reactor effluent may be recycled to extinction and thereby increase the overall yield of VCM. In practice, as indicated in FIG. 1, the reactor effluent recovered from the fluid bed reactor is treated to recover VCM, HCl and ethylene and then the remaining fraction of the effluent is recycled to the reactor for introduction to the fluidized bed of solids together with fresh EDC. It also is contemplated that the bottoms fraction from the vinyl chloride column 54 may be treated to separate out any tar-like residues or polymerized vinyl chloride before being recycled to the fluid bed reactor. Also, although it is preferred to feed substantially pure EDC to the fluid bed reactor from the oxyhydrochlorination reactor, it is contemplated that the EDC from such source may contain small amounts of other chlorinated ethylene compounds as impurities.

Examples III-V show that the addition of carbon tetrachloride is more beneficial with respect to EDC conversion to VCM than the addition of chlorine.

Examples VI and VII show that the addition of carbon tetrachloride to ethylene reduces the extent of equipment pluggage from carbon.

Example VIII shows (by comparison with Example I) that EDC conversion is lower if carbon tetrachloride is not added to the feed for reactor 2 and if by-products recovered from the effluent of reactor 2 are not recycled back to the reactor via line 56 as shown.

It is to be appreciated that the present invention may be utilized to effect production of other alkyl halides and conjoint dehydrohalogenation of such other alkyl halides to a corresponding halogenated unsaturated hydrocarbon. The halogen substituent of the alkyl halide may consist, for example, of chloride, bromine or iodine. The process also lends itself to the treatment of tri- as well as di-halo substituted hydrocarbons. By way of example, the following halogenated hydrocarbons, all of which (as is well known in the art) may be pyrolytically dehydrohalogenated, may be used in place of EDC to form a corresponding halogenated unsaturated hydrocarbon: 1,1 dichloroethane, trichloroethanes, di- and tri-chloropropanes, di- and tri-chlorobutanes, di-bromoethanes, di- and tri-bromopropanes, di- and tri-bromobutanes, and higher boiling saturated alkyl chlorides and bromides having at least two halogen atoms in the molecule. More than one alkyl halide may be produced and dehydrohalogenated simultaneously. Production of halogenated unsaturated hydrocarbons via pyrolytic dehydrohalogenation of alkyl halides is exemplified by British Pat. No. 1,218,417 and U.S. Pat. Nos. 2,569,923, 2,378,859, 2,379,372, 2,838,577, and the references cited therein.

In addition to the advantages already mentioned, the present invention entails lower capital equipment costs and requires less real estate than a balanced complex of the type described by Buckley. Also, the invention provides a substantial reduction in utilities cost and water consumption. In fact, the use of the fluid bed reactor makes it possible for a system as shown in FIG. 1 to be a producer rather than a consumer of steam. Because of the recycling of by-products, the problem of waste disposal is reduced substantially.

The invention is susceptible of a number of modifications. Thus, for example, more than one riser (or transfer line) may be employed in reactor 2, if desired. Still other modifications will be obvious to persons skilled in the art.

What is claimed is:

1. Apparatus for producing vinyl chloride monomer, said apparatus comprising in combination:
a reaction vessel, a bed of non-catalytic solids in said reaction vessel, means for feeding ethylene dichloride into said reaction vessel so as to fluidize said bed of solids, at least one solid transfer line connected at one end to a solids exit port in the bottom of said reaction vessel and at the opposite end to a solids reentry port in the side of said reaction vessel, a plurality of chlorine injection ports spaced along said solids transfer line between its ends, and means for feeding ethylene into said line adjacent the end connected to said solids exit port so as to cause solids to circulate from the bottom of said bed into and through said line and into the side of said reaction vessel, so that heat produced by the reaction of ethylene and chlorine in said solids transfer line can be absorbed by said circulating solids and carried into said reaction vessel, means for removing a reaction products effluent from said reaction vessel, means for separately recovering hydrogen chloride and vinyl chloride from the effluent withdrawn from said reaction vessel,
an oxyhydrochlorination reactor containing an oxyhydrochlorination catalyst, means defining a source of ethylene, a source of oxygen and means defining a source of hydrogen chloride, means connecting said sources of ethylene, oxygen and hydrogen chloride respectively to means for feeding ethylene, oxygen and hydrogen chloride to said oxyhydrochlorination reactor for contact with said oxyhydrochlorination catalyst whereby to form ethylene dichloride, means for removing the oxyhydrochlorination reaction effluent from said oxyhydrochlorination reactor, and means for recovering ethylene dichloride from the effluent removed from said oxyhydrochlorination reaction effluent and delivering said recovered ethylene dichloride to said means for feeding ethylene dichloride to said reaction vessel.

2. Apparatus according to claim 1 wherein said solids reentry port is located above the level of said bed.

3. Apparatus according to claim 1 wherein said solids reentry port is located at a level between the top and bottom of said bed.

4. Apparatus according to claim 1 further including means for delivering the hydrogen chloride recovered from the reaction effluent withdrawn from said reaction vessel to said means for feeding hydrogen chloride to said oxyhydrochlorination reactor.

5. Apparatus according to claim 1 wherein said non-catalytic solids have a surface area of less than about 50 square meters per gram.

6. Apparatus according to claim 1 wherein said non-catalytic solids are selected from the group consisting of silica, alumina, silica-alumina, glass powder and carbon solids of about 50-70 microns average diameter.

7. Apparatus for producing vinyl chloride monomer comprising means defining a first reaction chamber, a bed of non-catalytic solids in said chamber, means defining a source of ethylene dichloride, means for feeding ethylene dichloride from said source into said first chamber so as to fluidize said bed of solids, at least one hollow riser made of a ceramic material and disposed in said first chamber having one end communicating with the bottom of said bed and an opposite end communicating with said first chamber at a level above the bottom of said bed, means defining a source of chlorine, means for feeding chlorine from said source into said riser at several points spaced along said riser between said one end and said opposite end of said riser, means defining a source of ethylene and means for feeding ethylene from said source into said one end of said riser so as to direct all of said ethylene into said riser and to cause solids to circulate from the bottom of said bed into said one end of said riser and from said opposite end of said riser back into said first chamber, whereby (a) ethylene and chlorine can react in said riser to produce ethylene dichloride and heat and (b) the circulating solids can absorb heat produced by said ethylene-chlorine reaction and give up said heat to the ethylene dichloride produced in said riser and the ethylene dichloride fed into said first chamber so as to produce vinyl chloride by dehydrochlorination of said ethylene dichloride, and means for removing reaction products from said first chamber.

8. Apparatus for producing vinyl chloride monomer comprising means defining a first reaction chamber, a bed of non-catalytic solids in said chamber, means defining a source of ethylene dichloride, means for feeding ethylene dichloride from said source into said first chamber so as to fluidize said bed of solids, at least one hollow riser disposed in said first chamber having one end communicating with the bottom of said bed and an opposite end communicating with said first chamber at a level above the bottom of said bed, said one end of said riser comprising a venturi mixing nozzle, means defining a source of chlorine, means for feeding chlorine from said source into said riser at several points spaced along said riser between said one end and said opposite end of said riser, means defining a source of ethylene and means for feeding ethylene from said source into said one end of said riser so as to direct all of said ethylene into said riser and to cause solids to circulate from the bottom of said bed into said one end of said riser and from said opposite end of said riser back into said first chamber, whereby (a) ethylene and chlorine can react in said riser to produce ethylene dichloride and heat and (b) the circulating solids can absorb heat produced by said ethylene-chlorine reaction and give up said heat to the ethylene dichloride produced in said riser and the ethylene dichloride fed into said first chamber so as to produce vinyl chloride by dehydrochlorination of said ethylene dichloride, and means for removing reaction products from said first chamber.

9. Apparatus for producing vinyl chloride monomer comprising means defining a first reaction chamber, a bed of non-catalytic solids in said chamber, means defining a source of ethylene dichloride, means for feeding ethylene dichloride from said source into said first chamber so as to fluidize said bed of solids, at least one hollow riser disposed in said first chamber having one end communicating with the bottom of said bed and an opposite end communicating with said first chamber at a level above the bottom of said bed, said opposite end of said riser comprising at least one horizontally directed discharge part for directing solids and gases laterally into said bed, means defining a source of chlorine, means for feeding chlorine from said source into said riser at several points spaced along said riser between said one end and said opposite end of said riser, means defining a source of ethylene and means for feeding ethylene from said source into said one end of said riser so as to direct all of said ethylene into said riser and to cause solids to circulate from the bottom of said bed into said one end of said riser and from said opposite end of said riser back into said first chamber, whereby (a) ethylene and chlorine can react in said riser to produce ethylene dichloride and heat and (b) the circulating solids can absorb heat produced by said ethylene-chlorine reaction and give up said heat to the ethylene dichloride produced in said riser and the ethylene dichloride fed into said first chamber so as to produce vinyl chloride by dehydrochlorination of said ethylene dichloride, and means for removing reaction products from said first chamber.

* * * * *

UNITED STATES PATENT AND TRADEMARK OFFICE
CERTIFICATE OF CORRECTION

PATENT NO. : 4230668

DATED : October 28, 1980

INVENTOR(S) : Harold R. Sheely et al

It is certified that error appears in the above-identified patent and that said Letters Patent are hereby corrected as shown below:

Claim 1, line 27, column 18, the words "means defining" should be inserted before the words "a source".

Signed and Sealed this

Twenty-seventh Day of January 1981

[SEAL]

Attest:

RENE D. TEGTMEYER

Attesting Officer    Acting Commissioner of Patents and Trademarks